(12) United States Patent
Maier et al.

(10) Patent No.: US 10,099,268 B2
(45) Date of Patent: Oct. 16, 2018

(54) METHOD FOR MANUFACTURING AN EXTRUSION DIE

(71) Applicant: WEFA Singen GmbH, Singen (DE)

(72) Inventors: Oliver Maier, Ranolfzell (DE); Joachim Maier, Singen (DE)

(73) Assignee: WEFA Singen GmbH, Singen (DE)

( * ) Notice: Subject to any disclaimer, the term of this patent is extended or adjusted under 35 U.S.C. 154(b) by 376 days.

(21) Appl. No.: 14/300,562

(22) Filed: Jun. 10, 2014

(65) Prior Publication Data

US 2014/0360247 A1  Dec. 11, 2014

(30) Foreign Application Priority Data

Jun. 10, 2013  (DE) .................. 10 2013 106 010

(51) Int. Cl.
| | |
|---|---|
| C23C 16/06 | (2006.01) |
| B21C 25/02 | (2006.01) |
| G01N 3/56 | (2006.01) |
| B23K 9/04 | (2006.01) |
| B23K 9/23 | (2006.01) |

(Continued)

(52) U.S. Cl.
CPC ............ B21C 25/02 (2013.01); B21C 25/025 (2013.01); B23K 9/04 (2013.01); B23K 9/23 (2013.01); B23K 28/02 (2013.01); B23P 15/24 (2013.01); G01N 3/56 (2013.01); *B23K 2203/04* (2013.01); *B23K 2203/08* (2013.01); *B23K 2203/18* (2013.01); *B23K 2203/26* (2015.10)

(58) Field of Classification Search
CPC ......... C23C 16/06; C23C 16/14; C23C 20/04; B05D 3/02
See application file for complete search history.

(56) References Cited

U.S. PATENT DOCUMENTS 4,533,389 A * 8/1985 Kapoor .................. C22C 45/008
                                                        148/328
4,574,459 A * 3/1986 Peters ................... B23P 15/243
                                                        29/460

(Continued)

FOREIGN PATENT DOCUMENTS

| EP | 1011885 A1 | 6/2000 |
|---|---|---|
| EP | 1011884 B1 | 11/2002 |

(Continued)

OTHER PUBLICATIONS

Kostic, Milivoje, et al., "Desgin of Extrusion Dies". Encyclopedia of Chemical Processing DOI: 10.1081/E-ECHP-120039324, 2006, 633-649.*

(Continued)

*Primary Examiner* — Bret P Chen
(74) *Attorney, Agent, or Firm* — Bachman & LaPointe, PC

(57) ABSTRACT

Method for producing an extrusion die having a functional surface for metal extrusion material, comprising the following steps: providing a die support body, depositing a weldable substance containing cobalt and/or nickel onto a subsection of the die support body by means of an effective bonding application process to produce an inseparable deposition layer, machining the deposition layer in a chipping and/or material removal process to form the functional surface of the extrusion die, and carrying out a CVD coating process with a reaction gas at least on the functional surface.

16 Claims, 2 Drawing Sheets

(51) Int. Cl.
*B23K 28/02* (2014.01)
*B23P 15/24* (2006.01)
*B23K 103/08* (2006.01)
*B23K 103/04* (2006.01)
*B23K 103/18* (2006.01)

(56) References Cited

U.S. PATENT DOCUMENTS

| | | | | |
|---|---|---|---|---|
| 5,242,644 | A * | 9/1993 | Thompson | D01D 5/253 |
| | | | | 264/177.15 |
| 5,860,305 | A | 1/1999 | Castricum | |
| 6,011,248 | A * | 1/2000 | Dennis | B22F 3/105 |
| | | | | 219/700 |
| 6,176,153 | B1 | 1/2001 | Maier | |
| 6,193,497 | B1 * | 2/2001 | Suzuki | B28B 3/269 |
| | | | | 264/177.12 |
| 6,370,934 | B1 | 4/2002 | Maier | |
| 2002/0094379 | A1 * | 7/2002 | Sung | C23C 16/01 |
| | | | | 427/249.8 |
| 2004/0263021 | A1 * | 12/2004 | Irwin | B29C 47/0019 |
| | | | | 310/215 |
| 2009/0028980 | A1 * | 1/2009 | Asaoka | B29C 47/0028 |
| | | | | 425/382 R |
| 2009/0218322 | A1 * | 9/2009 | Folmar | B23H 9/00 |
| | | | | 219/69.17 |
| 2010/0189592 | A1 * | 7/2010 | Angles | C22C 38/12 |
| | | | | 420/110 |
| 2011/0159279 | A1 * | 6/2011 | Kobayashi | B21C 25/025 |
| | | | | 428/336 |
| 2013/0192328 | A1 * | 8/2013 | Hiramoto | B21C 25/02 |
| | | | | 72/273 |
| 2014/0147590 | A1 | 5/2014 | Maier et al. | |

FOREIGN PATENT DOCUMENTS

| | | |
|---|---|---|
| WO | 98/46377 A1 | 10/1998 |
| WO | 2012175147 A1 | 12/2012 |

OTHER PUBLICATIONS

Altan, Taylan, et al., "Selection of Die Materials and Surface Treatments for Increasing Die Life in Hot and Warm Forging". submitted to 28th Forging Industry Conference, Chigago, IL, Apr. 5-6, 2011, pp. 1-32.*
Borowski, J., et al., "The Phenomenon of Durability Variable Dies for Aluminum Extrusion Profiles". Metalurgija 55 (2016) 2, 229-232.*
Garza, Daniel, et al., "Improvement of Tool Life of Aluminum Extrusion Die Tools". Tribologia, Mar. 2013, 151-166.*
German Patent Office Action for Application DE 102013106010.2 dated Apr. 24, 2014.

* cited by examiner

METHOD FOR MANUFACTURING AN EXTRUSION DIE

BACKGROUND OF THE INVENTION

The present invention relates to the field of extrusion die engineering, and in this field to a method for manufacturing an extrusion die. A suitable substance for extrusion, typically an aluminium alloy, is forced under high pressure through an aperture that is delimited by an extrusion die, and during this extrusion process and while passing through the die, the substance has a ductile, highly viscous consistency such that it may be formed into a suitable, even complex shape configuration, depending on the design of the extrusion die.

Due to the special circumstances associated with extrusion technology, most importantly the fact that the ductile extrusion substance advances continuously over the (stationary) functional surface of the tool under high pressure and at high temperature, particular requirements must be imposed on both the design of the tool and the material from which the tool is constructed. Firstly, the functional surface that constitutes the contact area with the extrusion substance must be exceptionally resistant to wear, a characteristic that is typically achieved by applying a coating that suitably increases the hardness of the surface, or by subjecting the substance to a surface hardening process (nitriding or the like). Secondly, the particular conditions of extrusion and the particular geometries (such as long tabs or thin crosspieces) of the extrusion shapes that are to be produced also demand that the tool possess a certain resistance, with the consequence that the use of very hard (but brittle) substances, hard metals or high speed steels for example, which would otherwise be conceivable, often proves impossible. The high operating temperatures in extrusion dies, typically between 550° C. and 640° C., also impose greater requirements on the steels used for the die in terms of resistance to prolonged heat, which in turn means that cold work steels, for example, lend themselves less readily to use in an extrusion die.

From the prior art, it is known and has proven a reliable way to increase the wear resistance (and thus also the service life) of an extrusion die, if a coating is applied in a CVD process. For example, EP 1 011 885 B1 by the same Applicant discloses a method for coating an extrusion die by means of high-temperature CVD, in which a metal phase is deposited (in otherwise known manner) on the surface of the suitably prepared and shaped die; a preferred processing temperature for such a process is above 950° C., in order to ensure optimum reactivity of the gases used for gas deposition.

From WO 2012/175147 A from the same Applicant, it is further known to coat an extrusion die by means of chemical gas phase deposition (CVD) in the "mid-temperature" range. Such a process, particularly with greater concentrations of carbon in the deposition gas, lends increased resilience and elasticity to the functional surface of the extrusion die (when it is coated in this way), which is advantageous for extrusion technology for the reasons stated in the introduction.

Finally, it is also known from the prior art to require the use of materials consisting of hard metals or non-ferrous alloys to produce an extrusion die. However, these materials are very brittle, and it is very difficult to shape them when making dies, with the result that these technologies have only found limited practical use.

A further drawback is that these materials are expensive, and it is seldom possible to create extrusion dies economically with them.

SUMMARY OF THE INVENTION

The object of the present invention is therefore to create a method for producing an extrusion die, and an extrusion die produced thereby, with further improved surface properties, particularly in the area of the heavily stressed functional surfaces, above all enabling still greater wear resistance compared with the technology according to EP 1 011 885 B1, which is considered to be representative of the species, thereby enabling longer service life in extruding operations, while ensuring that the characteristics of the die include adequate resistance and low brittleness, for low material costs.

The object is solved by the method having the features disclosed herein, advantageous refinements of the invention are also described herein. Protection within the scope of the present invention is also claimed in particular for an extrusion die that is produced by the method according to the invention for processing aluminium-based extrusion material, wherein the present invention is also intended to be applicable for other extrusion materials, particularly extrusion metals. Further protection according to the invention is also claimed for a method for measuring surface wear of an extrusion die, particularly an extrusion die according to the invention, although protection might also be justifiably claimed for such a measuring method on its own merits.

Advantageously for the purposes of the invention, the method according to the invention primarily provides that a deposition layer is applied in an effective application process to a die support body made from a hot work steel that has been suitably shaped and/or machined to yield a die blank. According to the invention, this deposition layer consists of a cobalt-containing material, in which case a non-ferrous alloy on a cobalt and/or nickel basis, particularly a cobalt-chromium basis, is preferred. Such substances are known commercially as Stellite® and are deposited on a subsection of the die support body that is involved in the creation of the functional surface by means of a (single- or multilayer) build-up welding process as the inventive deposition process.

According to the invention, after this production of the deposition layer, said layer undergoes a finishing process to create the final shape of the functional surface, by appropriate chipping and/or material removal, for example, wherein erosion methods such as spark erosion have proven particularly suitable for shaping the functional surface from the deposition layer for typical dimensions.

Further according to the invention, this machining step is followed by a CVD coating process of at least the machined functional surface, so that said surface, already consisting of a typically high strength, highly wear resistant, cobalt-containing substance, also receives a CVD coating to further improve the wear behaviour thereof.

Thus, within the scope of the invention it has been found to be surprisingly effective if the cobalt-containing substance that constitutes the functional surface (the Stellite, for example) interacts synergistically with the CVD coating (typically containing Ti, Zr, B, Cr, Cu, Mg, $Al_2O_3$ or Hf as the coating metal), thus combining the excellent internal stress properties of the coated material with positive wear resistance behaviour.

To this extent, the present invention enables the production of extrusion dies that offer significantly longer service lives and thus render additional application areas (and other extrusion substances) economically accessible to the already highly advanced extrusion technology.

At the same time, not only does the scope of the invention encompass the underlying ability to produce an extrusion die by means of the method according to the invention, the scope of the inventive "production process" must also be considered to include handling existing tools, such as extrusion dies in the sense of repairing or overhauling them, by applying the inventive steps, and thereby enabling (potentially valuable) extrusion dies to be reused or recycled.

Advantageously with regard to further development, it has proven beneficial to subject the die support body to a thermal treatment before the step of removing the deposition layer by chipping or material removal, in order to reduce material stresses. Such stress relief heat treatment (which may be carried out in addition or alternatively to the chipping or material removal step for forming the functional surface) enables particularly good adhesion of the deposition layer, thus enhancing the synergistic effect.

It has also proven to be an advantageous development of the invention if the die support body is subjected to thermal pretreatment before the deposition layer is produced, that is to say before the cobalt-containing material is applied, by build-up welding, for example. Such thermal pretreatment is preferably conducted in a temperature range between 400° C. and 700° C., thus typically reaching a lower annealing temperature of a hot work steel that is preferably used for producing the die support body. Particularly from the point of view of process control, it has proven advantageous for refinement purposes to carry out the heat treatment steps to be performed on the die support body for subsequent development before the deposition layer is applied and/or to carry out the machining or material removal processes on the die support body with the deposition layer applied in a shielding gas atmosphere; this helps to prevent the occurrence of undesirable reactions or surface effects.

Within the scope of the invention, the inventive deposition of the CVD coating may be carried out either as a medium-temperature process (that is to say with a coating temperature between about 700° C. and about 950° C.), or as a high-temperature process (that is to say with a typical coating temperature above 950° C., preferably above 1000° C.). A particularly preferred variant of the CVD coating process within the scope of the invention consists in applying the CVD coating in multiple layers, in such manner that a covering layer is deposited by high-temperature CVD on top of a (suitably resistant) medium-temperature CVD layer. Regarding the specific parameters of such coating processes, reference is made to the further disclosure of WO 2012/175147 by the same Applicant, which for the present purpose is to be considered associated with the invention and to be included in the present disclosure.

Consequently, the present invention constitutes a surprisingly effective method, with limited manufacturing effort (and financially favourable use of materials, as before), for producing extrusion dies having outstanding resistance to wear, wherein the present invention offers the capability to repair or refurbish existing tools with the technology according to the invention above and beyond the simple production of new dies.

BRIEF DESCRIPTION OF THE DRAWINGS

Additional advantages, features and particularities of the invention will be evident from the following description of preferred embodiments and with reference to the drawing, in which.

DETAILED DESCRIPTION

Figure 1:
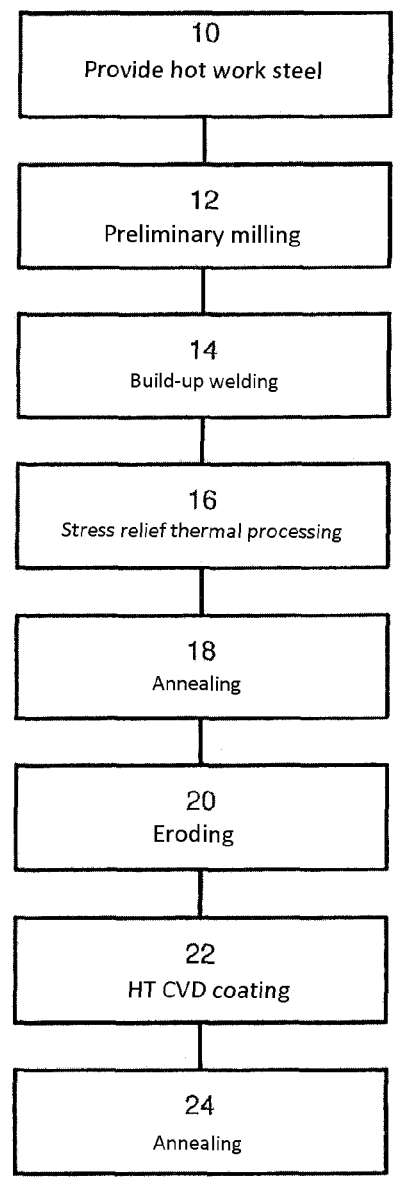
FIG. 1: is a schematic flowchart showing the process steps of the method for producing an extrusion die according to a preferred embodiment of the invention.

In the following, the method according to a first preferred embodiment of the invention for producing an extrusion die having a functional surface for metal extrusion material will be described with reference to FIGS. 1 to 3; FIG. 1 indicates the sequence of process steps 10 to 24.

Figure 2:
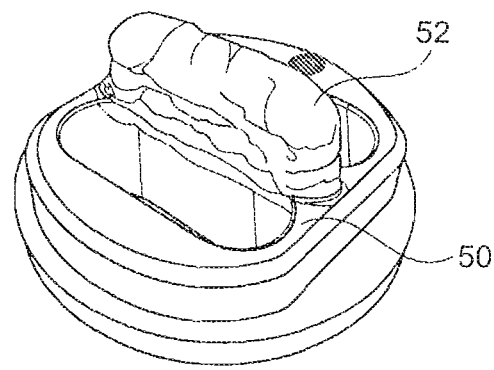
FIG. 2: is a perspective view of an extrusion die after the process of depositing a cobalt-containing substance according to the method of FIG. 1.
Figure 3:
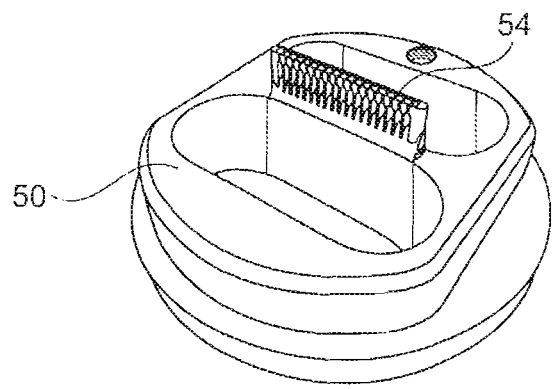
FIG. 3: is a perspective view of the extrusion die of FIG. 2 after the machining removal process of the cobalt-containing substance deposited according to FIG. 2.

According to the embodiment described, in step 10 a hot work steel is provided, and in step 12 a tool form is produced in a material removal process; for this purpose, the embodiment of FIGS. 2 and 3 shows a mandrel tool that is constructed in cooperation with a matrix tool (not shown) for extruding an aluminium profile. The hot work steel is type 1.2344 steel; a maximum diameter of the tool shown in various stages of production in FIGS. 2 and 3 is approximately 45 mm.

The material removal machining (step 12) is followed by multilayer build-up welding with a cobalt-containing material of type Stellite 6, available commercially from the company Kennametal, for example.

This multilayer build-up welding is typically carried out at a temperature of 650° C., wherein the build-up welding (not shown in the workflow diagram in FIG. 1) may be preceded by a heat treatment step, at a temperature of 550° C.-700° C. for an hour, for example.

FIG. 2 shows the result after depositing of the cobalt-containing material, designated with reference sign 52, and joined inseparably to the underlying tool body (die support body) 50 made from hot work steel by build-up welding.

In the subsequent step 16, stress relief heat treatment of the configuration shown in FIG. 2 at 550° C.-700° C. is carried out over a period of about two hours. This is followed by a further heat treatment step 18, for annealing (at a typical annealing temperature) of about 580° C. to 600° C. for example. This heat treatment step 18 is advantageous, but is not essential for obtaining the advantages of the invention.

These treatment steps are followed by the chipping or material removal processing of deposition layer 52 in functional surfaces 54, as shown in FIG. 3. In this embodiment according to the invention, this process has the form of spark erosion with the objective of forming the functional surface according to desired contour or actual structure (in the embodiment shown, for producing intermediate ribs in an extrusion product). The result of this material removal step is shown in FIG. 3.

In the context of the embodiment according to the invention, this is followed by a CVD coating step, process step 22, which is applied at least to area 54 where the material was applied and subsequently removed in a chipping or material removal process, in practical terms this being the entire die. In otherwise known manner, as disclosed in the referenced prior art of EP 1 011 885 B1 for example, $Al_2O_3$ for example is deposited from the gas phase at a typical high temperature CVD coating temperature of 1050° C., and thus creates a coating on the functional surface or the die. Subsequent annealing (step 24) to a typical annealing temperature in the range of about 500° C.-600° C. completes the production process and delivers the finished extrusion die.

In practice, it has proven favourably that compared with tools according to EP 1 011 885 B1 that have undergone CVD coating and are otherwise of identical construction, wear resistance results may be improved by 30% to 50%, which is reflected in a correspondingly longer operating and service life of the tool.

Figure 4:
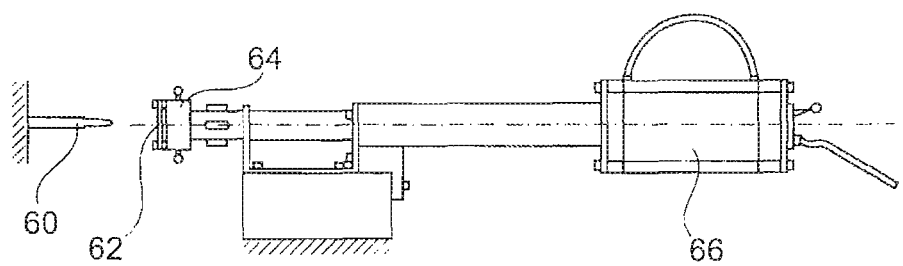
FIG. 4: is a schematic side view of a test device for conducting a wear test for extrusion dies produced according to the present invention.

In order to obtain such comparative data, it has proven preferable to use a device such as is illustrated diagrammatically in FIG. 4, which serves to generate wear data, particularly of extrusion dies coated in a CVD process and enables assessments of wear resistance properties to be made for comparison purposes. Specifically for this purpose, as shown schematically in the left part of FIG. 4, a sample 60 (produced from a hot work steel and treated with the subsequent process steps 12 to 24 according to the invention) is fixed in non-rotating manner and brought into contact with a friction partner 62 made from an aluminium alloy and secured in a carrier unit 64, which is rotated under pressure by a rotary drive unit 66 and brought into contact with sample 60 to produce the friction. In the present case, the interaction takes place at rotating speeds between 40 and 100 rpm and under a contact pressure of about 2 to 8 bar; in this configuration, care must be taken to ensure that the temperature of friction partner 62 (which has the form of an interior cone corresponding to the cone-shaped contour of sample 60) does not exceed an operating temperature of about 300° C., which might result in the friction partner melting or otherwise becoming unusable.

Now, if test readings are taken after various periods, and a point in time is determined at which the tool (sample 60) reaches the wear limit (because pieces of the tool or support body become detached, for example), a value becomes available that can be used under comparable test conditions to evaluate the advantages of the present invention in relative measurement readings with respect to the extrusion dies coated by species-related CVD coating methods.

Independent protection is claimed within the scope of the present invention for the method of carrying out such a comparative wear test and an arrangement of the kind illustrated in FIG. 4.

The invention claimed is:

1. Method for producing metal extrusion die having a functional surface for metal extrusion material, comprising the following steps:
   providing (10) a die support body (50) comprising hot work steel,
   depositing (14) a weldable substance containing cobalt and/or nickel onto a subsection of the die support body by means of an effective bonding application process to produce an inseparable deposition layer (52),
   machining (20) the deposition layer in a chipping and/or material removal process to form the functional surface (54) of the extrusion die, and
   carrying out a CVD coating process (22) with a reaction gas at least on the functional surface.

2. Method according to claim 1, wherein the effective bonding application process has the form of single- or multilayer build-up welding (14).

3. Method according to claim 1, wherein the die support body with the applied deposition layer undergoes heat treatment (16).

4. Method according to claim 3, wherein the heat treatment process reduces internal stresses before the machining operation for chipping and/or material removal.

5. Method according to claim 1, wherein the machining operation for chipping and/or material removal is carried out by milling or eroding in a spark erosion process (20).

6. Method according to claim 1, wherein a preliminary forming and/or preliminary chipping operation (12) is carried out on the die support body in the area of the subsection, before the deposition layer is created.

7. Method according to claim 1, wherein the die support body undergoes a preheating step, to a temperature between 400° C. and 700° C. and/or to an annealing temperature of the hot work steel before the deposition layer is created.

8. Method according to claim 1, wherein the die support body is preheated before the cobalt-containing material is applied and/or the die support body furnished with the deposition layer undergoes a stress relief heat treatment.

9. Method according to claim 1, wherein the welding material is a non-ferrous alloy having a cobalt base and/or a nickel base.

10. Method according to claim 9, wherein the cobalt base is a cobalt-chromium base.

11. Method according to claim 1, further comprising a heat treatment (24) of the die support body after the CVD coating process at an annealing temperature.

12. Method according to claim 1, wherein the CVD coating process is carried out as a medium-temperature process at a coating temperature in a range between 700° C. and 950° C.

13. Method according to claim 1, wherein the CVD coating process is carried out at a coating temperature above 1000° C.

14. Method according to claim 1, wherein the extrusion die is produced as a tool comprising two parts, having a mandrel part and a die plate and the inseparable application layer is applied to at least sections of both the mandrel part and the die plate.

15. Method according to claim 1, wherein the functional surface is created as the delimiting wall of the extrusion die defining a guide and/or flow channel for the ductile extrusion substance.

16. Method according to claim 1, wherein the CVD coating process is carried out as a medium-temperature process at a coating temperature in a range between 700° C. and 950° C., followed by a high-temperature process at a coating temperature above 950° C., in order to create a covering layer on top of a CVD coating that is produced by the medium-temperature process.

* * * * *